United States Patent [19]

Deer

[11] Patent Number: 4,878,379
[45] Date of Patent: Nov. 7, 1989

[54] RHEOMETER

[75] Inventor: John J. Deer, Epsom, United Kingdom

[73] Assignee: Carri-Med Ltd., Worthing, United Kingdom

[21] Appl. No.: 799,778

[22] PCT Filed: Oct. 16, 1986

[86] PCT No.: PCT/GB86/00625
§ 371 Date: Jun. 3, 1987
§ 102(e) Date: Jun. 3, 1987

[87] PCT Pub. No.: WO87/02458
PCT Pub. Date: Apr. 23, 1987

[30] Foreign Application Priority Data
Oct. 17, 1985 [GB] United Kingdom ............ 8525662

[51] Int. Cl.$^4$ .................................................. G01N 3/24
[52] U.S. Cl. ................................................ 73/60; 73/843; 374/46
[58] Field of Search ............... 73/60, 843; 374/46, 374/48, 53

[56] References Cited

U.S. PATENT DOCUMENTS 2,574,715  11/1951  Sontag ........................... 73/60 X
3,479,858  11/1969  Umeno et al. ................. 73/843 X
3,535,914  10/1970  Veith et al. .

FOREIGN PATENT DOCUMENTS 2308926  11/1976  France ............................ 374/46
52-15387  2/1977  Japan ............................. 374/46

Primary Examiner—Stewart J. Levy
Assistant Examiner—Joseph W. Roskos
Attorney, Agent, or Firm—Dennison, Meserole, Pollack & Scheiner

[57] ABSTRACT

A rheometer having relatively movable shearing elements (4,5) for imposing shear forces on a sample of material placed between such elements, is provided with heating means comprising an induction heating coil (18) heated to permit induction heating of the elements (4,5) during use.

15 Claims, 3 Drawing Sheets

RHEOMETER

This invention relates to rheometers. The term "rheometers" includes not only viscometers but also instruments for determining elastic or plastic deformation of samples of material. By means of suitable rheometers measurements can be made of the elastic or plastic deformation of solid and semi-solid materials under predetermined forces and of the elastic or plastic deformation of flowable materials under forces insufficient to bring about continuous flow as measurable by a viscometer. Some rheometers are capable of measuring the deformation of samples of flowable material through the viscoelastic range and into the continuous flow region to enable elastic or plastic deformation as well as viscosity readings to be obtained from the one instrument.

The invention is particularly concerned with rheometers comprising relatively displaceable elements (hereafter called "shearing elements") for subjecting an intervening sample of material to shear forces, and more particularly to so-called rotation rheometers in which the relative displacement of the elements is rotational, whether unidirectional or oscillatory or a combination of both.

For a rheometer reading to be fully reliable the sample must be at a known temperature at the time the measurement is made. It is therefore important for the temperature of the sample to be controllable. Many rheological measurements have to be made while the sample is kept heated to a predetermined temperature above the environmental temperature.

Most prior art rheometers for testing samples at elevated temperature are provided with heating means for heating the environment around the shearing elements. In some rheometers the shearing elements are cylindrical elements arranged one inside the other and heat is supplied by heated water which is circulated through a heating jacket surrounding the outer element [cf e.g. the article entitled "A concentric cylinder air turbine viscometer" by S. S. Davis, J. J. Deer and B. Warburton in Journal of Scientific Instruments (Journal of Physics E) 1968 Series 2 Volume 1, pp 933–935]. In other known rheometers, the shearing elements are operated within a convection oven.

It is also known to employ an electrical resistance heating system using a heating resistor incorporated into a fixed shearing element.

The prior art rheometers are satisfactory for certain measurement purposes but their range of practical usefulness is restricted by heating and temperature control factors. There is an increasing requirement for rheological tests to be performed at temperatures well above those for which existing rheometers are suited. For example there is need for various synthetic polymers to be tested at temperatures much higher than 150° C. Heating of materials to such high temperatures by means of rheometer heating systems of the known kinds would take much more time than can be afforded in many testing laboratories. Moreover testing would have to be restricted to materials which are not impaired by retention at the high temperatures for the time which would be necessary.

One object of the present invention is to provide a rheometer having a heating system by which samples of material can be economically heated even to temperatures well above 150° C. in a very short time.

According to the present invention there is provided a rheometer comprising two elements ("shearing elements") between which a sample of material to be tested can be located, means for relatively displacing said elements so as to subject a said sample to (a) controlled shear force(s), means for heating the sample to a controlled extent, and means for automatically indicating a deformation or flow parameter of the material under the applied force(s), characterised in that there is at least one said shearing element which is made of or includes electrically conductive material and the heating means comprises an induction heater having at least one induction heating coil or loop located to permit induction heating of that electrically conductive material.

The invention utilises the induction heating principle in circumstances which are unlike those in which it is conventionally practised. Rheometers of the kinds with which the invention is concerned are used for testing very small representative samples of material. For rheological measurement purposes, samples in the range 20–40 ml are generally considered very large. Measurements are usually made on samples less than 10 ml in volume and the present invention is primarily concerned with instruments capable of testing samples within that size range. The shearing elements of such rheometers are in consequence of very small dimensions. The gap between the two elements, in which the sample is acommodated, is typically of the order of 2 mm or less. It has been found that despite the special circumstances, the application of an induction heating technique is a practical proposition. By appropriate selection of electric current frequencies and other factors, a highly efficient, economic induction heating system can be provided which gives the rheometer important performance advantages over the prior art rheometers hereinbefore referred to.

The invention enables the provision of a rheometer in which samples of material to be tested can be heated to high test temperatures more quickly than in the prior art instruments. The invention is not restricted to rheometers suitable for high temperature work. Indeed, an induction heating system can be used for tests at controlled temperature in the ordinary ambient temperature range, or even for temperature control purposes in an instrument having sample cooling means for testing samples at temperatures below ambient or even below 0° C. However the invention is primarily intended for application to instruments capable of testing samples at elevated temperatures, and particularly at temperatures above 150° C. It is in relation to such high temperature testing that the benefit of heating time reduction is most evident. With a suitably designed induction heating system, sample temperatures as high as 400° C. can be reached in a matter of a few minutes. It is quite feasible to make a rheometer according to this invention by which rheological measurements can be made on molten glass.

Heating by means of an induction heating system can be sensitively and easily regulated as compared with heating by conduction from a water bath or other surrounding heating medium. In contrast to resistance heating systems, an induction heating system does not involve fire hazards when testing volatile substances. Yet another potential advantage is that the induction heating system is ideally suited to the heating of a moving shearing element because the heat is generated directly in such element without physical contact with the heating energy source. This is of particular importance for certain rheometers, e.g. rotational controlled stress rheometers, wherein the frictional resistance to rotation of one of the rotatable shearing elements should be virtually nil. That element is normally supported by an air bearing or air bearings. The present invention enables such a rotary shearing element, whatever its physical form, to be directly inductively heated without any loss of the benefits of using frictionless bearings.

Another advantage is that the generated heat is so efficiently used that thermal insulation around the inductively heated shearing element(s) can be dispensed with. Heat losses can be negligible. Should only one of the elements be inductively heated the other element can itself be of insulating material.

The present invention can be applied to any form of rheometer for determining material deformation or flow under shear forces applied by contacting relatively moving shearing elements. Such rheometers can be of various constructions depending on the kinds of materials to be tested and on which parameter or parameters is or are to constitute the predetermined input factor(s) characterising the applied shear forces. As is well known in the art, rheological measurements can be made on the basis of a predetermined shear rate or on the basis of a controlled constant shear stress input. For determining sample deformation in the viscoelastic region a constant shear stress rheometer is used (see the above cited article in JSI 1968 Series 2 Volume 1, at pp 922). Constant shear rate and constant stress rheometers can comprise upper and lower shearing elements, one of which is driven at a constant rate or subjeced to a constant torque as the case may be. And the deformation of the sample can be measured in terms of the torque transmitted to the other element via the sample or in terms of the angular displacement of that other element. Examples of commerically available rheometers of the different kinds referred to are the R20 range of Weissenberg Rheogoniometers marketed by Carri-Med Limited, of Dorking, Surrey, England and the Rheometrics (Trade Mark) Stress Rheometer marketed by Rheometric Inc. of Piscatawa, N.J., U.S.A. and Rheometrics GmgH of Frankfurt, West Germany.

In preferred embodiments of the invention the rheometer is a rotational rheometer, i.e. a rheometer in which the shear forces are applied by subjecting at least one of the shearing elements to rotary motion (unidirectional or oscillatory) relative to the other element.

The invention is also applicable to other forms of rheometer wherein the sample material is subjected to shear forces by relatively moving shearing elements. Examples of such rheometers are falling bar and falling band viscometers (see e.g. the article entitle "Measurement and control of viscosity and related flow properties" by R. McKennel in "Instrumental Manual", 1960, Section 11). In such other forms of instrument the inductive generation of heat directly within the falling body will promote greater accuracy in the determination of rheological data.

In certain particularly preferred embodiments of the invention, to which particular importance is attached, the induction heating circuit is self-tuning in dependence on the impedance of the circuit, which includes the inductively heated element(s). As known per se, automatic tuning can be achieved by means of a power factor correction feedback system or phase lock loop. For versatility of use it highly desirable to use a rheometer which can be fitted with shearing elements of different dimensions or of different forms and dimensions to suit the particular sample to be tested and the rheological data to be derived from the rheometer. In a rotational rheometer employing shearing elements of parallel plate or nested cone type or in the form of inner and outer co-axial cylinders, both elements should be easily removable and replaceable by elements of other design specification. By using a self-tuning circuit, the efficient performance of the heating circuit is not dependent on the dimensions and geometry of the inductively heating shearing element(s) and these can be changed from time to time to suit the work in hand.

Another factor of importance for keeping power requirements within reasonable limits for a small laboratory instrument is the frequency range of the heating current. Despite the small size of the shearing elements, the inductively heated material of the or each element should be confined to a surface stratum or skin which contacts the sample being tested. In general, the heating circuit should be capable of operating at a heating current frequency such that the or each heated shearing element can be inductively skin-heated to a depth of less than 3.0 mm and in most cases the skin heating depth should be very appreciably less than that value. Preferably the skin heating depth is less than 0.5 mm and most preferably less than 0.3 mm. Generally speaking, coil current frequencies in the range 10 to 300 KHz are suitable for skin heating the elements to depths in the range 3.0 mm to 0.15 mm. The rheometer can incorporate a facility for varying the coil current frequency e.g. to permit the skin heating depth to be varied or to allow for different air gaps between the induction heating coil and the shearing elements consequent upon the use of shearing elements of substantially different diameters. The skin heating depth may for example need to be varied if an ordinary shearing element is substituted by a very thin element as used in surface rheology.

In the most important embodiments of the invention, both shearing elements are directly inductively heated. This feature is of much importance for promoting uniform heating of the entire volume of a sample undergoing test. It is much easier to avoid significant temperature gradients across the sample than in the case of prior art rheometers employing a heating bath or a resistance heater incorporated into one of the shearing elements. The heating bath principle is only suitable in the case of a rheometer utilising concentric cylinder type shearing elements and in such cases it is of course only the outer shearing element which is exposed to the heating medium. In the case of resistance heating, the heating resistor can only be conveniently incorporated in a fixed shearing element.

In particularly advantageous embodiments of the invention, wherein the induction heater is arranged for inductively heating both shearing elements as above referred to, the induction heater functions to inductively heat both shearing elements by means of a common induction coil; the energy absorbing properties of said elements are such that they are heated to substantially the same temperature for any given power level to the inductive heating circuit; a temperature sensor is incorporated in a surface region of one of said shearing elements; and said sensor is connected to the induction heater so that said power level is automatically controlled in dependence on an output signal from said sensor. This combination of features makes an important contribution to the accuracy of measurement which can be achieved by means of the rheometer.

In such a rheometer, the temperature sensor is preferably incorporated in a shearing element adjacent the face thereof which makes contact with the sample when the rheometer is in use. It is of course most suitable to incorporate the temperature sensor in a fixed, or at least non-driven, shearing element. A platinum resistance thermometer can for example be used as the temperature sensor.

While it is far more advantageous for both of the shearing elements to be inductively heated, the invention is not restricted to rheometers having that feature. For some rheological test puposes, sufficiently reliable results can be achieved if only one of the shearing elements is inductively heated. The other element can being heated indirectly by heat conduction through the sample and/or by radiation. In the case of inner and outer co-axial cylindrical shearing elements, the inner element can be inductively heated and the outer element can be of thermally insulating material.

The shearing elements can be of any suitable geometric form. Various forms of shearing elements useful in rotational rheometers are known in the art, e.g. co-axial cylinders, and elements of parallel plate or nesting cone type as already referred to. In the case that elements in the form that co-axial cylindrical elements are used they can if required both be inductively heated by means of a coil surrounding the outer element. For example the outer element can incorporate inductively heatable material in one or more annular zones within the length of the cylinder.

In order for a given shearing element to be inductively heatable it is not necessary for it to be made entirely of metal. It can for example be of a composite form comprising a non-metallic body bearing a metallic cladding. And it is also possible to use different metals for different parts of a shearing element. For example each shearing element can comprise a core or body of a metal of high thermal conductivity, such as copper, and a cladding of a metal of lower electrical conductivity, such as chromium.

The invention includes a method of measuring a rheological property of a sample of material of a volume not more than 10 ml by locating the sample between shearing elements of a rotational rheometer, applying shear force(s) to said sample via said elements while they are heated to a predetermined temperature, and deriving an indication of said rheological property from an output signal of a measuring circuit, characterised in that the shearing elements employed are inductively skin-heated by means of a common induction heating coil to a depth of less than 3.0 mm, the energy absorbing characteristics of said elements being such that their temperatures are thereby kept substantially equal; the skin temperature of at least one of said shearing elements is measured by a temperature sensor delivering a signal indicative of the measured temperature; and said sensor signal is used for controlling the induction heating current thereby to control the temperature of the sample. The frequency of the induction heating current is preferbly such that said shearing elements are skin-heated to a depth of less than 0.5 mm and most preferably less than 0.3 mm.

Certain embodiments of the invention will now be described with reference to the accompanying diagrammatic drawings, in which.

Figure 1:
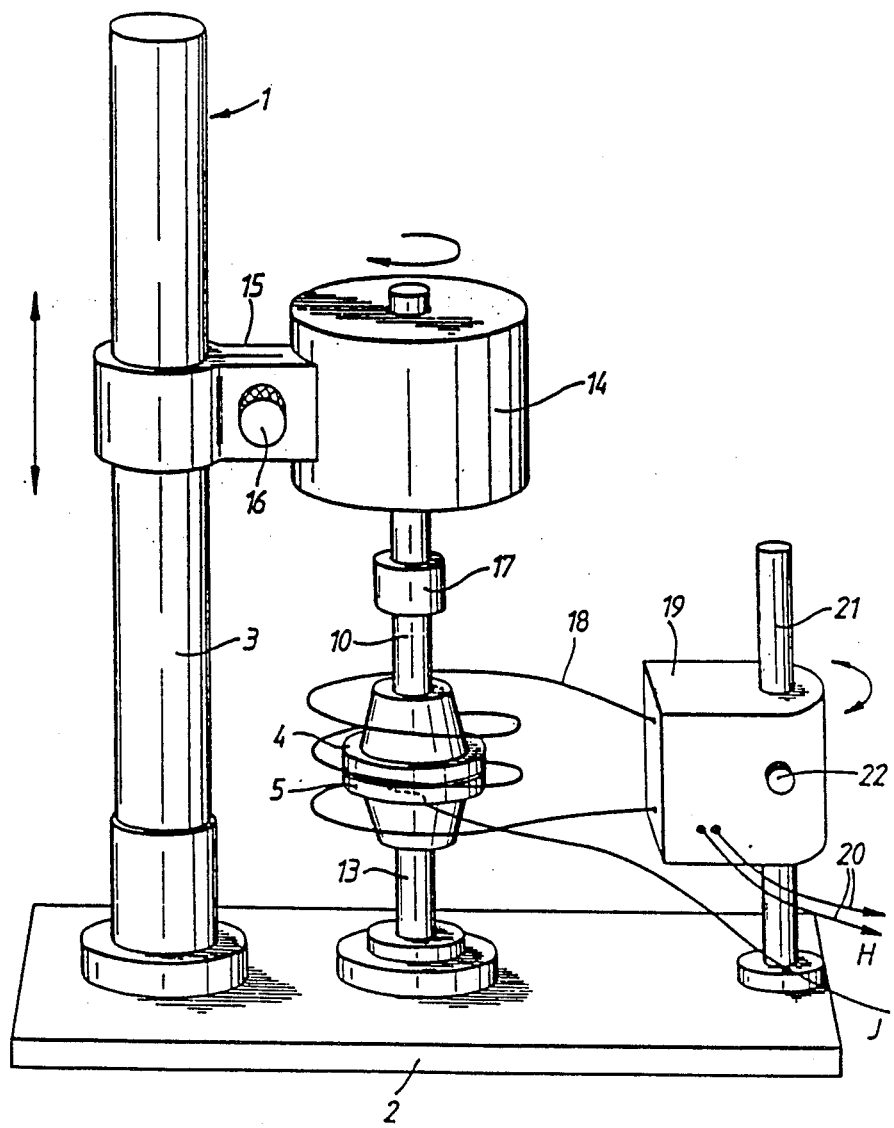
FIG. 1 is an elevation of a rheological measuring instrument embodying the present invention.
Figure 2:
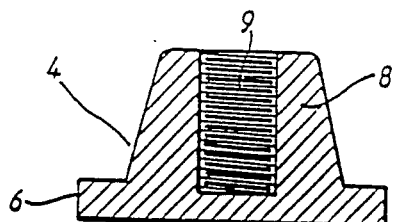
FIG. 2 is a cross-sectional elevation of a shearing element.

The instrument represented in FIG. 1 is a controlled constant shear stress rheometer. The instrument comprises a stand 1 having a base 2 and a pillar 3. The instrument incorporates shearing elements 4 and 5 of parallel plate type. FIG. 2 is a cross-sectional elevation of the upper shearing element 4. It comprises a disc portion 6, which provides the flat sample-contacting face 7 of the element, and an integral hub portion 8 which has a threaded socket 9 for connection to spindle 10.

Figure 3:
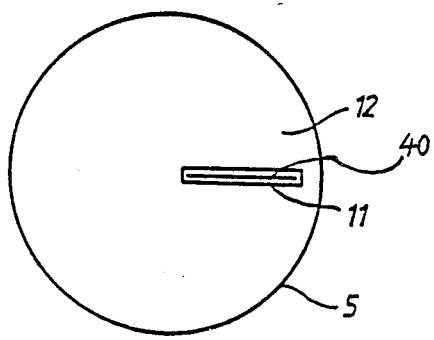
FIG. 3 is a plan view of a shearing element.

The lower shearing element 5 is of similar form to element 4 except that it has accommodation for a temperature sensor. FIG. 3 is a plan view of this lower shearing element. It has a radial groove 11 in its flat sample-contacting face 12. A platinum resistance thermometer 40 is installed in this groove. The lower shearing element is screwed onto a support 13 fixed to the base 2.

A controlled torque can be applied to the spinle 10 by means of an electric motor 14. Motor 14 is connected to the pillar 3 by a clamping bracket 15 to which clamping force is applied by a bolt 16. When this bolt is loosened the bracket can be slidden upwardly along the pillar thereby to retract the rotatable shearing element 4 away from the fixed element 5 to permit a sample of material to be placed on the fixed element. The element 4, with its driving motor, can then be lowered into a position in which the shearing elements are spaced by a gap of the required thickness, ready for the test.

The spindle 10 incorporates a body 17 of thermally insulating material which provides a thermal break between the shearing element 4 and its driving motor.

The heating means comprises an inductive heating coil 18 which is connected within a junction box 19 with current conductors 20 which connect the coil into a induction heater circuit hereinafter described. The junction box 19 is releasably secured to a post 21 by means of a fastener 22. When the upper shearing element 4 is in its retracted position, this fastener can be released and the junction box together with coil 18 can be raised and turned around the post 21 so as to swing the coil away from the fixed shearing element 5 and allow unobstructed access thereto.

Different forms of shearing elements can be fitted in place of elements 4 and 5 to suit different types of sample.

The instrument includes measuring means (not shown) for measuring the extent of angular displacement of the shearing element 4 for a given controlled constant torque applied to the spindle 10 when the shearing elements and therefore the sample undergoing test are at (a) predetermined temperature(s). This angular displacement is a function of the temperature-dependent deformation of the sample material within the viscoelastic range. Suitable angular displacement measuring means for this purpose are known in the art. Such a measuring means in used in the Rheometrics (Trade Mark) Stress Rheometer hereinbefore referred to.

An instrument of a general form similar to that illustrated in FIG. 1 can be designed for measuring the viscosity of a film of a Newtonian fluid material at various temperatures. For example such an instrument can have a lower shearing element mounted for angular displacement against a torsional resistance, means for turning the upper shearing element at a constant angular velocity and means for measuring the torque transmitted to the lower element by the fluid. A suitable type of measuring means for that purpose is used in the Weissenberg Rheogoniometers hereinbefore referred to.

Figure 4:
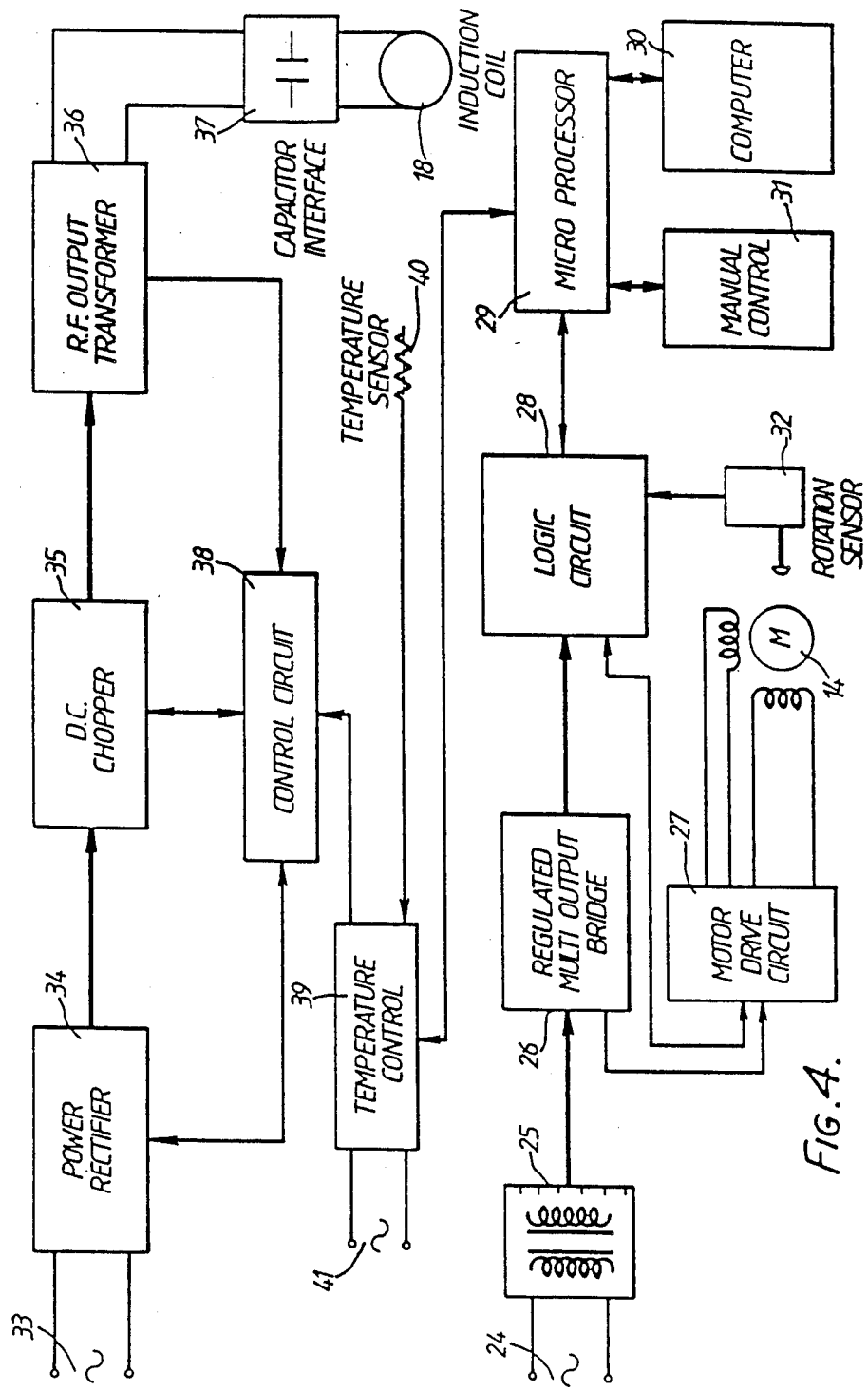
FIG. 4 is a block diagram of the heating and measuring circuits of the rheometer shown in FIG. 1.

Details of the heating and measuring circuitry of the controlled stress rheometer represented in FIG. 1 will now be described with reference to FIG. 4.

The lower part of the diagram represents the rheometer drive circuitry which is functionally interconnected with the induction heater circuitry represented in the upper part of the diagram.

Input terminals 24 are for connection to an alternating current source providing power for operating the electric motor 14 which applies torque to the spindle 10 carrying the upper shearing element 4 (FIG. 1). Between those input terminals and the motor 14 there is a multi-way transformer 25, and a multi-output rectifier bridge 26 which is connected to the motor drive circuit 27. The bridge 26 is connected by a multi cable to a logic circuit 28 which collects and directs signals from and to a microprocessor 29, and from and to the motor drive circuit 27. The microprocessor is linked with a programmed computer 30 and with a manual control means 31 which can be used instead of the computer.

The motor drive circuit provides a two-phase output current of a frequency in excess of 100Hz at the voltage which will result in application of torque of the required value, to the spindle 10. This torque value is determined to suit the particular rheological test in hand and the appropriate voltage for establishing that torque is set automatically by the computer 30 or by means of the manual control means 31. The electric motor 14 is of the "drag-cup" type which under the control of its drive circuit provides a constant output torque.

The extent or rate of angular displacement of the spindle 10 in response to the constant applied torque is detected by a rotation sensor 32. The measured rotation of the spindle, in conjunction with the constant torque value, is used as a measure of the shear resistance of the sample material at the temperature which it has at the time of the measurement. The sensor signals, and signals indicative of the applied torque, are fed to the computer 30 for automatic analysis, or to means yielding a visual record or display of values for subsequent analysis, in terms of rheological data.

The sample temperature at which any given measurement is made is determined and controlled by the induction heating system to which a separate source of EMF is connected via input terminals 33. These terminals are connected to a power rectifier 34 from which direct current feeds to a D.C. chopper 35. The chopper delivers an alternating current of complex wave form to an R.F. transformer 36 the output side of which is connected to the induction heating coil 18 via a capacitor interface 37.

As already indicated, shearing elements of different dimensions can be fitted to the rheometer. The impedance of the heating circuit depends in part on the dimensions of the shearing elements for the time being in use. In order to ensure that the heating circuit is in resonance, whatever the dimensions of those elements, the induction heating circuit must be self-tuning. This is achieved by means of the tuning lock feedback link from the R.F. transformer 36 to a control circuit 38. This control circuit is linked to a temperature control 39 which is coupled to the platinum resistance thermometer 40. This thermometer is located in the lower shearing element 5 close to its sample-contacting face, as described with reference to FIG. 3. The control circuit 38 can be operated by manual control in dependence on a temperature indicator linked to the thermometer 40, so as to maintain a required temperature or to follow a required temperature-v-time schedule. Alternatively the temperature control 39 can be pre-set so that the control circuit is automatically regulated by the temperature control in dependence on output signals from the thermometer 40. The control circuit 38 is coupled with the power rectifier 34 so that the circuit 38 controls the power supply to the induction heating coil 18. The coil current frequency remains constant. If desired, a different frequency can be achieved by suitable modification of the electronic circuitry. Alternatively a frequency adjustment facility can be built into the system. If desired, a different The temperature control 39 is connected to a separate voltage source via terminals 41 so that electrical interference from other parts of the instrument is avoided.

The temperature control 39 can if desired be operated from the computer via the logic circuit as is represented by the double arrowed connections.

Figure 5:
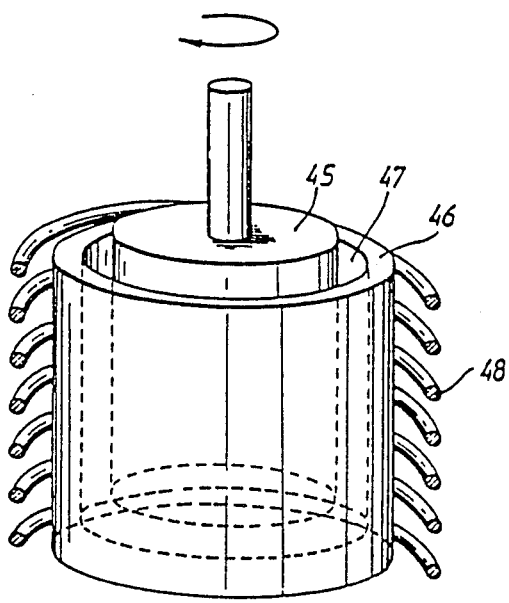
FIG. 5 shows part of another rheometer according to the invention.

FIG. 5 shows the shearing elements and associated heating coil of another rheometer according to the invention. The shearing elements 45 and 46 are of coaxial cylinder type, defining an annular gap 47 for the sample to be tested. The heating coil 48 surrounds the outer element. Both of the shearing elements can be inductively heatable. For example the inner element 45 can be of stainless steel and the outer element 46 can have stainless steel bands which are spaced apart along its length and are exposed to the annular gap 47. As an alternative the outer element can be made entirely of a thermally insulating material, heating of the sample being achieved solely by inductive heating of the inner element.

The following are examples of technical specifications of a rheometer as described with reference to FIGS. 1 to 4, and of the use of such an instrument:

EXAMPLE 1

The rheometer was used for testing a sample of glass-filled nylon, over a temperature range from ambient to 385° C. For the purpose of the test, parallel plate shearing elements 4 and 5 formed of chrome plated copper (plating thickness 0.172 mm) and having a diameter of 4 cm were used. The energy-absorbing characteristics of the two elements were the same. The test was conducted with the shearing elements at a spacing of 1mm. The induction heating coil was formed from 6 mm diameter copper tubing through which cooling water was passed. The coil had an internal diameter of 65 mm.

The power supply to the heating coil was initially set to supply a current of 2.1 amp at 270 V (meter readings), corresponding with an approximate power consumption of 550 W. The current frequency was 200 KHz. Optimum performance of the circuit was ensured by virtue of its self-tuning, i.e. its auto-regulation to resonance. The temperature of the shearing element 5 as measured by the platinum resistance thermometer 40 increased from ambient temperature to 300° C. in 210 seconds, at the end of which time the power supply became automatically reduced by the control circuit to approximately 125W and held at that value for 60 seconds. The "overshoot" of the 300° C. temperature setting was less than 0.2%. The power supply was then increased to its original value of 550W. Under this power the temperature increased from 300° C. to 385° C. in about 100 seconds. The power supply then reduced to between 125 and 150W. The temperature was held at 385° C. just long enough for a steady angular displacement reading (as hereafter referred to) to be obtained. Because the two shearing elements had the same energy absorbing characteristics it was certain that the two elements were always at the same temperature.

The motor drive circuit 27 was switched on at the start of the heating period above referred to and the driving power was regulated to apply a constant stress of 5000 dyne.cm. Angular displacement of the shearing element 4 under this applied torque, as detected by the rotation sensor 32 and signalled thereby to the computer 30, first occurred at a temperature of about 275° C. and increased as the temperature continued to rise. A displacement rate of 0.006 radians per second was recorded during the time the temperature reading was 300° C. The displacement rate thereafter increased with the rise of temperature, reaching 0.01 radians per second at 385° C. The sample was subject to chemical change or degradation at temperatures above 350° C. Displacement values recorded within that high temperature range can therefore be instructive of the degradation process.

The test demonstrates the very rapid heating of the shearing elements to high temperatures for a very modest power consumption. The reliability of the recorded rheological data is of a very high order due to the fact that the shearing elements are at equal temperatures throughout the test and the consequent absence of disturbing temperature gradients within the sample.

EXAMPLE 2

The instrument used in Example 1 was used for deriving rheological data for white polyethylene during heating up to a temperature of 175° C.

The shearing elements employed were identical with those used in Example 1 and the spacings of the elements from each other and from the induction heating coil were also the same as in that example.

The power in the heating circuit was initially set as in Example 1 and was reduced to 40 to 50W when the maximum temperature of 175° C. was reached.

A constant torque of 3000 dyn.cm was applied to shearing element 4 as soon as the induction heating circuit was switched on. Angular displacement of the shearing element started to occur at a temperature of 140° C. as measured by the thermometer 40 and reached a recorded rate of 0.005 radians per second at 175° C.

We claim:

1. A rotational rheometer comprising two shearing elements between which a sample of material to be tested can be located, means for applying a rotational force to at least one of said elements so as to subject a sample between said elements to a controlled shear force, means for heating the sample to a controlled extent, and means for automatically indicating a deformation or flow parameter of the material under the applied force, at least one said shearing element comprising electrically conductive material and the heating means comprising an induction heater having at least one induction heating coil or loop located to permit induction heating of said electrically conductive material.

2. A rheometer according to claim 1, wherein said heating means and said at least one shearing element comprise an induction heating circuit which is self-tuning in dependence on the impedance of the circuit.

3. A rheometer according to claim 1 or 2, wherein the induction heater is capable of generating an inductive heating current in a frequency range such that the inductively heated material of the at least one shearing element is confined to surface layers only of said element.

4. A rheometer according to claim 3, wherein the induction heater is capable of generating an inductive heating current at frequencies such that the at least one shearing element is skin-heated to a depth of less than 3.0 mm.

5. A rheometer according to claim 4, wherein the induction heater capable of generating an induction heating current at at least one frequency within the range 10 to 300 KHz.

6. A rheometer according to claim 5, wherein both shearing elements are directly inductively heatable by said heating means.

7. A rheometer according to claim 4, wherein said depth is less than 0.5 mm.

8. A rheometer according to claim 1, wherein both shearing elements comprise electrically conductive material.

9. A rheometer according to claim 8, wherein the induction heater functions to inductively heat both shearing elements by means of a common induction loop or coil; the energy absorbing properties of said elements are such that they are heated to substantially the same temperature for any given power level to the induction heating circuit; a temperature sensor is incorporated in an inductively heated surface region of one of said shearing elements and said sensor is connected to the induction heater so that said power level is automatically controlled in dependence on an output signal from said sensor.

10. A rheometer according to claim 9, wherein the temperature sensor is incorporated in at least one shearing element adjacent the face thereof which makes contact with the sample when the rheometer is in use.

11. A rheometer according to claim 10, wherein the temperature sensor is located in a non-driven shearing element.

12. A rheometer according to claim 9, wherein each shearing element is of composite form comprising a body of metal of high thermal conductivity clad with a skin of a metal of lower thermal and electrically conductivity than said body.

13. A method of measuring a rheological property of a sample of material of a volume not more than 10 ml by locating the sample between shearing elements of a rotational rheometer, applying a shear force to said sample via said elements while they are heated to a predetermined temperature, and deriving an indication of said rheological property from an output signal of a measuring circuit, wherein the shearing elements employed are inductively skin-heated to a depth of less than 3.0 mm by means of an induction heater comprising at least one induction heating coil, the energy absorbing characteristics of said elements being such that their temperatures are thereby kept substantially equal; the skin temperature of one of said shearing elements is measured by a temperature sensor delivering a signal indicative of the measured temperature; and the induction heating current is controlled in dependence on said sensor signal thereby to control the temperature of the sample.

14. A method according to claim 13, wherein the shearing elements are inductively skin-heated in contact with the sample by means of said induction heating coil to a depth of less than 0.5 mm.

15. A method according to claim 13, wherein a common induction heating coil is used to heat said shearing elements.

* * * * *